US00PP22961P2

(12) United States Plant Patent
Mack

(10) Patent No.: US PP22,961 P2
(45) Date of Patent: Aug. 14, 2012

(54) ***PHLOX* PLANT NAMED 'THAI PINK JADE'**

(50) Latin Name: *Phlox paniculata*
Varietal Denomination: Thai Pink Jade

(75) Inventor: Tasanee S. Mack, Annapolis, MD (US)

(73) Assignee: Plants Nouveau, LLC, Charleston, NC (US)

( * ) Notice: Subject to any disclaimer, the term of this patent is extended or adjusted under 35 U.S.C. 154(b) by 63 days.

(21) Appl. No.: 12/928,175

(22) Filed: Dec. 6, 2010

(51) Int. Cl.
*A01H 5/00* (2006.01)

(52) U.S. Cl. ..... Plt./320

(58) Field of Classification Search ..... Plt./320
See application file for complete search history.

*Primary Examiner* — June Hwu
(74) *Attorney, Agent, or Firm* — Penny J. Aguirre

(57) ABSTRACT

A new and distinct cultivar of *Phlox* plant named 'Thai Pink Jade' characterized by its compact and bushy plant habit, its strong dark colored stems, its medium green foliage, its long lasting porcelain pink colored flowers with a small dark pink eye, and its resistance to powdery mildew.

2 Drawing Sheets

Botanical classification: *Phlox paniculata.*
Cultivar designation: 'Thai Pink Jade'.

BACKGROUND OF THE INVENTION

The present invention relates to a new and distinct cultivar of *Phlox* plant, botanically known as *Phlox paniculata* 'Thai Pink Jade' and will be referred to hereafter by its cultivar name, 'Thai Pink Jade'. The new cultivar represents a new herbaceous perennial grown for landscape use.

The new cultivar of *Phlox* was discovered as a naturally occurring whole plant mutation by the Inventor in a garden planted with numerous cultivars of *Phlox paniculata* in Annapolis, Md. in July 2006. The parentage is unknown.

Asexual reproduction of the new cultivar was first accomplished by stem cuttings under the direction of the Inventor in Union, Ill. in July 2006. It has been determined that the characteristics of this cultivar are stable and are reproduced true to type in successive generations.

SUMMARY OF THE INVENTION

The following traits have been repeatedly observed and are determined to be the unique characteristics of 'Thai Pink Jade'. These characteristics in combination distinguish 'Thai Pink Jade' as a new and distinct cultivar of *Phlox.*

1. 'Thai Pink Jade' exhibits a compact and bushy plant habit.
2. 'Thai Pink Jade' exhibits strong stems that are dark colored in spring.
3. 'Thai Pink Jade' exhibits clean, medium green leaves.
4. 'Thai Pink Jade' exhibits pale pink colored flowers with a dark pink eye.
5. 'Thai Pink Jade' exhibits a very high degree of resistance to powdery mildew.

Plants of the new *Phlox* can be compared to plants of *Phlox paniculata* 'Franz Schubert' (not patented). Plants of the new *Phlox* and 'Franz Schubert' differ primarily in the following characteristics: 1. Plants of the new *Phlox* have darker colored foliage than 'Franz Schubert'. 2. Flowers of plants of the new *Phlox* have spatulate shaped flower petals that do not overlap, where the flower petals of 'Franz Schubert' do overlap. 3. Plants of the new *Phlox* are much more resistant to powdery mildew than plants of 'Franz Schubert'.

Plants of the new *Phlox* can also be compared to plants of *Phlox paniculata* 'Eva Cullum' (not patented). Plants of the new *Phlox* and 'Eva Cullum' differ primarily in the following characteristics: 1. Plants of the new *Phlox* are much shorter than plants of 'Eva Cullum'. 2. Flowers of plants of the new *Phlox* have spatulate shaped flower petals that do not overlap, where the flower petals of 'Eva Cullum' do overlap. 3. Plants of the new *Phlox* are much more resistant to powdery mildew than plants of 'Eva Cullum'. 4. Plants of the new *Phlox* have medium, clear pink flowers with a dark pink eye whereas the flowers of 'Eva Cullum' are clear pink with a maroon eye.

BRIEF DESCRIPTION OF THE DRAWING

The accompanying colored photographs illustrate the overall appearance and distinct characteristics of the new *Phlox*. The photographs were taken of a three year-old plant of 'Thai Pink Jade' as grown in a garden in Landenberg, Pa.

The photograph in FIG. 1 comprises a side perspective view of a flowering stem of 'Thai Pink Jade'.

Figure 1:
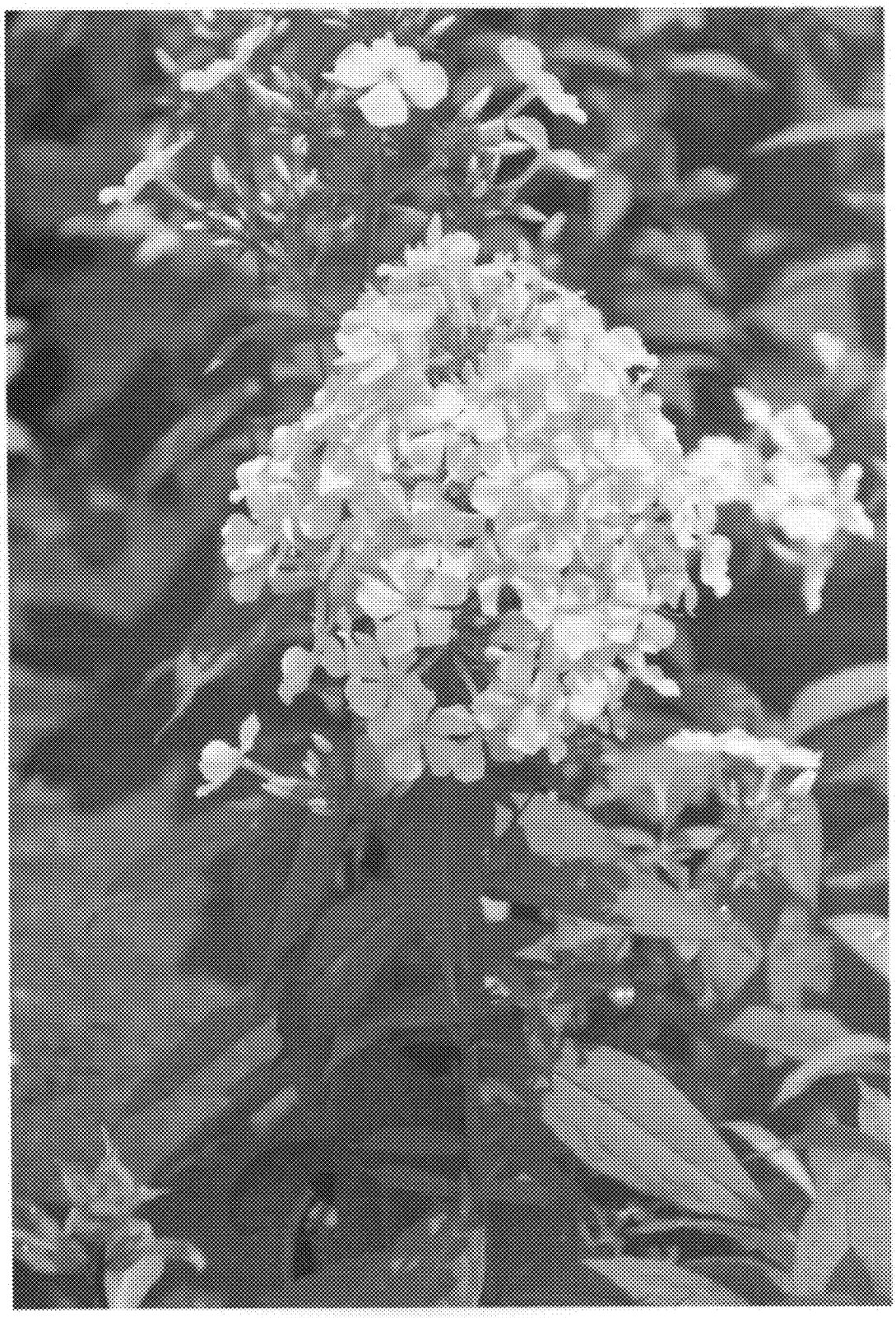
Figure 2:
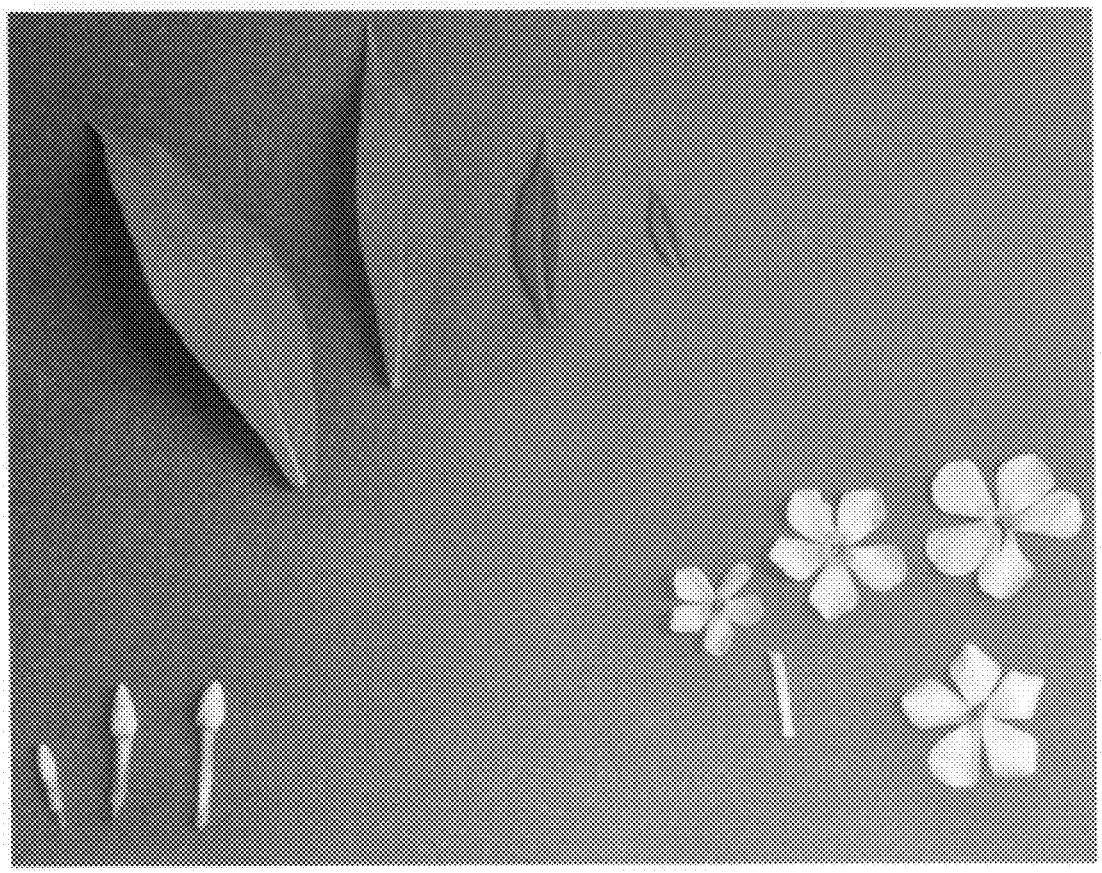

The photograph in FIG. 2 provides a close-up view of typical flowers (lower right), flower buds (lower left) and foliage (upper left) of 'Thai Pink Jade'. The colors in the photograph may differ slightly from the color values cited in the detailed botanical description, which accurately describe the colors of the new *Phlox.*

DETAILED BOTANICAL DESCRIPTION OF THE PLANT

The following is a detailed description of three year-old plants of the new cultivar as grown outdoors in a garden in Baltimore, Md. The plants were grown under average day temperatures of 23° C. to 40° C. and average night temperatures of 15° C. to 32° C. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period*.—Continuously from June to August in Baltimore, Md.

*Plant habit*.—Herbaceous perennial, compact, bushy.

*Height and spread*.—Reaches about 65 cm in height and about 50 cm in spread.

*Hardiness*.—Tolerant to temperatures ranging from −20° C. to 40° C.

*Environmental stresses*.—Good garden performance with tolerance to rain and wind.

*Diseases and pests*.—Has shown very good resistance to powdery mildew.

*Root description*.—Moderate branching, dense, fibrous.

Growth and propagation:

*Growth rate*.—Moderate.

*Propagation*.—Stem cuttings.

*Time to initiate roots*.—About two weeks at 15° C. to 25° C.

*Time to produce a rooted young plant*.—About 35 days at 15° C. to 25° C.

Stem description:

*Stem size*.—An average of 23 cm in length and 4 mm in width.

*Stem shape*.—Round.

*Stem strength*.—Strong and sturdy.

*Stem color*.—Spring: N79A, summer and fall: close to 144B with spots of N79A.

*Stem surface*.—Glabrous, smooth.

*Stem aspect*.—Held nearly upright.

*Internode length*.—An average of 3 cm.

*Branching habit*.—Flowering stems emerge from crown, an average of 5 stems per plant three years in age, pinching enhances branching.

Foliage description:

*Leaf shape*.—Narrowly ovate to elliptic.

*Leaf division*.—Simple.

*Leaf base*.—Obtuse.

*Leaf apex*.—Narrowly acute.

*Leaf venation*.—Pinnate.

*Leaf margins*.—Very finely serrate.

*Leaf attachment*.—Petiolate.

*Leaf arrangement*.—Opposite.

*Leaf size*.—An average of 9.5 cm in length and 3.5 cm in width.

*Leaf fragrance*.—None.

*Leaf surface*.—Smooth and glabrous on upper and lower surface.

*Leaf color*.—Developing leaves upper surface; about 137B with venation close to 144A, developing leaves lower surface; about 147B with venation about 145C, fully expanded leaves upper surface; about 146A, venation close to 148D, fully expanded leaves lower surface; about 147B, venation close to 145C.

*Petioles*.—Length; about 3 mm, diameter; about 2 mm, texture on upper and lower surfaces; smooth, glabrous, color upper and lower surfaces; close to 144D.

Flower description:

*Inflorescence type*.—Compound terminal panicle of single rotate flowers, panicle rounded in shape.

*Lastingness of inflorescence*.—About 4 weeks from the opening of the first flower to senescence of last flower, individual flower lasts about 10 days, not persistent.

*Inflorescence size*.—An average of 10 cm in height and 8 cm in diameter.

*Flower fragrance*.—Intense, sweet and flowery.

*Flower number*.—Average of 150 per inflorescence, one inflorescence per flowering stem.

*Flower aspect*.—Primarily outward.

*Flower bud*.—An average of 1.1 cm in length and up to 3 mm in width, narrow oblanceolate in shape, 75D with striations of 77C in color.

*Flower form*.—Explanate with tubular base.

*Flower size*.—An average of 2.5 cm in length and 2.2 cm in diameter.

*Corolla tube*.—About 15 cm in length, 3 mm in width, close to 77B on developing flowers and 75A on mature flowers, smooth surface.

*Corolla lobes*.—5, roughly spatulate in shape, held horizontally when fully open, not overlapping, about 1.6 cm in length and 1.2 cm in width, apex rounded, base fused to tube, entire margins, surface smooth and glabrous, color developing petals, upper surface; close to 69D with striations of 72C and close to N74B towards the throat, color developing petals, lower surface; 75D with striations of 77C, fully expanded petals, upper surface; close to 69D and close to 72A towards the throat, fully expanded lower surface; 69D.

*Sepals*.—5, fused towards base, lanceolate in shape, margins entire, apex narrowly apiculate, an average of 8 mm in length and 2 mm in width, surface is smooth and glabrous, color on developing flowers upper surface and lower surface; close to 149D, color on fully open flowers upper and lower surface; close to 142C with striations of 77A.

*Peduncles*.—Length; about 6 cm, diameter; about 3 mm, strength; strong, texture; smooth, glabrous, 144C with striations of 144A in color.

*Pedicels*.—Length: about 5 mm, diameter; about 1 mm, strength; strong, texture; smooth, glabrous, close to 142C in color.

Reproductive organs:

*Gynoecium*.—1 pistil, about 1.2 cm in length, stigma is three parted and close to 145C in color, style is about 3 mm in length and close to 145C in color, ovary is inferior and close to 143B in color.

*Androecium*.—Typically 5 stamens, anthers are basifixed, oblong in shape, 3 mm in length and 2D in color, filaments are about 5 mm in length, pollen is moderate in quantity and close to 11C in color.

*Fruit and seeds*.—Development has not been observed.

It is claimed:

1. A new and distinct cultivar of *Phlox* plant named 'Thai Pink Jade' as herein illustrated and described.

* * * * *